United States Patent [19] [11] Patent Number: 4,840,706
Campbell [45] Date of Patent: Jun. 20, 1989

[54] METHOD AND APPARATUS FOR MEASURING WATER CONTENT

[75] Inventor: Neil F. Campbell, Canterbury, England

[73] Assignee: The Wiggins Teape Group Limited, Basingstoke, England

[21] Appl. No.: 15,592

[22] Filed: Feb. 17, 1987

Related U.S. Application Data

[63] Continuation of Ser. No. 654,684, Sep. 26, 1984, abandoned.

[30] Foreign Application Priority Data

Sep. 26, 1983 [GB] United Kingdom ............... 8325691

[51] Int. Cl.$^4$ ..................... D21F 7/06; G01N 21/17
[52] U.S. Cl. ................................. 162/198; 162/263; 162/DIG. 6; 250/339
[58] Field of Search ............... 250/339; 162/263, 198, 162/258, DIG. 6

[56] References Cited

U.S. PATENT DOCUMENTS

| 3,207,901 | 9/1965 | Barker, Jr. | 250/339 |
| 3,214,845 | 11/1965 | Huffman | 34/48 |
| 3,596,071 | 7/1971 | Doening | 162/263 |
| 3,619,359 | 11/1971 | Keyes, IV | 162/DIG. 6 |
| 3,821,553 | 6/1974 | French | 250/339 |
| 3,879,607 | 4/1975 | Bjorklund | 250/252 |
| 4,006,358 | 2/1977 | Howarth | 162/263 |

FOREIGN PATENT DOCUMENTS

| 1598467 | 3/1972 | Fed. Rep. of Germany . |
| 2044443 | of 0000 | United Kingdom . |
| 1013171 | 12/1965 | United Kingdom . |
| 1271439 | 4/1972 | United Kingdom . |
| 1373807 | 11/1974 | United Kingdom . |

OTHER PUBLICATIONS

Measurex brochure "Single-Sided Infrared Moisture Sensor", 1978.
Wallace, "Dryer Section Energy Use Reduced up to 15% with Computer Control", Pulp & Paper (May 1980).
Howarth, "Moisture Testing Verification", Measurex Technical Note.
Measurex brochure "DynaCO Intelligent Sensor 2255", 1980.
Mercer, "Improved Infrared Moisture Measuring Techniques", 1978.

Primary Examiner—Steve Alvo
Attorney, Agent, or Firm—Burns, Doane, Swecker & Mathis

[57] ABSTRACT

A modified infra-red scanning gauge used in measuring the moisture content of a paper-web during manufacture or when subject to a coating practice, has a measurement channel and a reference channel. The measurement channel is based on the infra-red absorption spectrum of water which has an absorption band centered on 1.94 microns. The reference channel is conventionally at a wavelength of 1.83 microns where water has previously been considered to be transparent to infra-red or at a wavelength of 1.68 microns. The gauge is intended for measurement of high water content, where at 1.94 microns absorption effectively becomes total thereby preventing measurement being made, and uses a narrow-band filter of 0.03 micron wavelength offset from the peak of the 1.94 micron absorption band in the range 1.76 to 1.87 microns, previously considered stable as regards water content but now disclosed as showing a water-dependent variation at high water contents. In a specific example a 1.83 micron filter is used for the measurement channel and 1.68 micron filter for the reference channel. The modified gauge which may be of the transmission or scatter type has particular use at the wet end of a paper-making machine.

18 Claims, 4 Drawing Sheets

METHOD AND APPARATUS FOR MEASURING WATER CONTENT

This application is a continuation of application Ser. No. 654,684, filed Sep. 26, 1984, now abandoned.

FIELD OF THE INVENTION

This invention relates to the measurement of the water content of a material and is particularly concerned with measurement by use of an infra-red spectroscopic technique. The invention is concerned with both a method and apparatus for such measurement.

The invention has particular application in papermaking and related fields such as manufacture of board materials. It may also find application generally to materials that are water-absorbent and are produced in sheet or web form, such as textiles. It may also find still more general application to other water-absorbent materials such as those manufactured in granular form particularly where they are moved on a conveyor and thus have a resemblance to a moving web of paper. The invention will be discussed and its practice described with specific reference to paper making.

BACKGROUND TO THE INVENTION

A typical paper-making machine for coated papers comprises in sequence: a Foudrinier wire; a press section; a main dryer section; a size press or on-machine coater; a further dryer section; and a reel-up section. The feedstock is applied to the wire upon which the web is formed and passes into the press section in which a substantial quantity of water is removed from the web. From the press section the still very wet web passes through the rolls of the main dryer section from which it emerges with a relatively low moisture content. The paper then passes into a size press or coater to receive its surface coating, and then passes through a further dryer to the reel-up roll.

If a non-coated paper is being manufactured then the size press or on-machine coater and the further drying section are omitted. In some cases the non-coated paper produced in this way is coated on a separate machine having one or more coating stations and dryer sections.

In some paper manufacture the main dryer section may be divided into two parts with an intermediate pair of smoothing rolls between the two parts.

The paper emerging from the main dryer section has a moisture content (water percentage by weight) of typically 5-10% dependent on the product and the moisture content of the paper as finally reeled-up is also typically in this range. A heavy paper has a grammage (weight in grams per square meter) of say 100 so that the grammage of water is up to 10 for the quoted moisture content. Clearly a much heavier product such as board would have a correspondingly higher grammage of water at the same moisture content.

It is conventional to measure moisture content on leaving the main dryer or at reel-up and such measurement may be used to adjust the machine operation toward achieving desired parameters. One technique for measuring moisture content is to utilize the absorption spectrum of water in the infra-red which exhibits a relatively sharp absorption waveband at a wavelength of 1.94 microns ($\mu$m). Monitoring or gauge apparatus for this purpose is commonly in use. Such apparatus conventionally uses either a fixed gauge or a gauge mounted on a scanning head which is repetitively scanned transversely across the web at the exit from the dryer section and/or upon entry to reel-up, as required by the individual machines. The gauges use a broadband infra-red source and one or more detectors (about which more is said below) with the wavelength of interest being selected by a narrow-band filter, for example an interference type filter. The gauges used fall into two main types: the transmissive type in which the source and detector are on opposite sides of the web and, in a scanning gauge, are scanned in synchronism across it, and the scatter type (sometimes called "reflective" type) in which the source and detector are in a single head on one side of the web, the detector responding to the amount of source radiation scattered from the web. It is important to note that the signal sensed by the detector is essentially a measure of water content, i.e. grammage of water. It does not give moisture content directly. The measurement at 1.94 $\mu$m is essentially due to water alone; it is not affected by the paper itself which is mainly cellulose.

To improve the operation of both types of gauge it is also the practice to ratio (or perform other compensating calculation of) the detector signal at 1.94 $\mu$m against a reference signal generated by detection at a wavelength at which water has little or no absorption of infra-red. As mentioned the absorption band at 1.94 microns is sharp and conveniently the reference wavelength is chosen at a shorter wavelength of about 1.83 $\mu$m (sometimes simply referred to as the 1.8 $\mu$m reference). 1.7 $\mu$m is used for the reference in some gauges. The reason for using the shorter rather than the longer wavelength side of the absorption band will become clear later. Measurements are commonly expressed in a converse form, namely in terms of the % transmission (transmissivity) at the selected wavelength which is inversely related to the absorption.

Without going into detail of the factors that affect the absolute value of the measurement at the selected absorption band (1.94 $\mu$m), it is sufficient to say that the ratio technique provides compensation for many factors that would otherwise produce errors in a measurement at a single wavelength.

The translation of the measurement of water content to one of moisture content requires a measure of the weight (grammage) of the web, either the paper or paper plus water, to which the water content can be related. Such a measurement can also be made with an infra-red gauge in that the infra-red absorption spectrum of cellulose, which is the major constituent of paper, has a well-defined absorption band at a wavelength that is adjacent and longer than that of the water absorption band. This wavelength is about 2.1 $\mu$m so that by use of an appropriate narrow-band filter at this wavelength a third detection signal can be obtained using the cellulose content as a measure of paper weight. As with the water measurement this cellulose absorption signal is preferably ratioed against a reference and in practice the 1.83 or 1.7 $\mu$m reference can serve for both, since at both wavelengths there is little absorption by cellulose. It will be realised that the water content reference wavelength is chosen on the short wavelength side to avoid interference that would otherwise arise from the nearby cellulose absorption band if a reference measurement were made on the longer wavelength side. The selection of a reference wavelength for other materials would have to be made with regard to the absorption spectrum for that material including its moisture content.

Alternatively the grammage of the sheet may be measured by a separate gauge using some other technique, such as the absorption of β-rays by the web. However measured, the grammage measurement is combined with the infra-red measurement of total water content by calculation to give the moisture content as a percentage, or as a ratio if preferred.

The statement just made that the response at 1.83 μm is little or not affected by water content is subject to an important qualification that will now be explained.

Scanning infra-red gauges of both the transmissive and scatter type are well established and have various refinements beyond the basic functions discussed above. Examples of numerous such gauges are the scatter type gauge available from Measurex Corporation in the United States under the model No. 2238, and the transmissive type gauge available with the 8012 control system from Paul Lippke GmbH. & Co. KG. in West Germany.

Further discussion of various factors influencing the measurement of water content by infra-red gauges can be found in U.S. Pat. No. 4,006,358 (Howarth) which discloses measurement at 1.94 μm against a 1.7 μm reference; and in British patent specification 2,044,443 which discloses measurement at 1.94 μm against a 1.8 μm reference, together with a cellulose measurement at 2.1 μm providing a correction value used in the calculation of moisture content. This specification is based on a proposition that the water content (weight per unit area) of a "film" is dependent on the absorption properties of other material in the film. Reference may also be had to a paper entitled "Improved Infrared Moisture Measuring Techniques" given by Peter G. Mercer at a symposium held at Maidstone, England on 11-12th Oct., 1978 by the Institute of Measurement and Control, and subsequently published by that Institute.

In making measurements at the various wavelengths mentioned it is the practice to use a narrow-band filter to select only the wavelength of interest. The bandwidth at 50% of peak transmission is typically 0.03 μm. Thus as will be better appreciated from the subsequent description, the spectrum region between 1.83 and 1.94 μm is relatively wide in terms of the filter bandwidths normally used and the wavebands are well separated.

British Patent Specification 1,013,171 includes a discussion on the tolerances acceptable in filters nominally operating at 1.94 μm. The specification discusses how far from the nominal centre-wavelength the filters may depart but is speaking of wider filters of 0.08 μm bandwidth where greater derivation from the nominal centre could be tolerated but is not preferred because of the loss of sensitivity to the wanted 1.94 μm wavelength.

It is noted that this specification is referring to filters available some twenty years or more ago. With present technology there is no difficulty in obtaining filters accurate in both bandwidths and nominal centre-wavelength so that a nominal 1.94 μm filter can be expected to be at that wavelength with a high degree of assurance.

Infra-red moisture gauges, of whatever type, have been customarily used at the dry end of paper machines, that is after the main drying section, where moisture content is relatively low, typically 5 to 10% for most grades of paper.

Recently there has been an increasing interest in measurement at the wet end of the machine. Typically, this involves a water to dry weight ratio (or "moisture ratio") of 4-6 (corresponding to a "moisture content" of 80-85.7%) in the web coming off the wire, and a moisture ratio of 1-3 following the press section. For a sheet with a dry weight of 100 grams/m$^2$, the grammage of water in the first instance would be 400-600 and in the second instance 100-300. Thus a completely different order of magnitude of measurement is required.

It is considered that in future more attention will have to be given to water content at the wet-end in establishing better control of the paper-making process and, for example, in avoiding the waste of energy in drying off water in excess of that required for proper production. The control at the wet end requires an on-line measurement of moisture content (the web here being generally predominantly water by weight) and a means for making such measurements reliably at the high water grammage abovementioned.

It is generally considered by suppliers of infra-red moisture gauges that they cannot be reliably used for water contents actually in paper in excess of a grammage of 25. This view is supported in the Mercer paper mentioned above. As reported in that paper, work has been done on water film alone to show that current gauges can measure up to 10 times that grammage of water on its own, i.e. measurements on a film of water. However, this is not a practical measurement and the large discrepancy with the figure quoted for water found as moisture in paper is due to the fact that in paper the infra-red radiation does not follow a straight line path but is multiply scattered by the fibres in the paper. The total absorption is proportional to total path length which is greatly increased by the scattering within the web. The detector signal thus represents the absorption over mean path length.

The difficulty is that as the absorption increases the signal to the detector decreases so that the detection limit is set by the noise and interference associated with the detector operation in the inherently noisy environment of a paper-making machine.

Consequently there would be a substantial advance if an infra-red spectroscopic technique were available to raise the practical limit for the measurement of water content in paper toward the 250 g/m$^2$ that has been quoted for pure water, let alone to the typical figure of 400-600 g/m$^2$ found in a web leaving the wire.

The high absorption, and low transmissivity, consequent upon an attempt to measure high water contents at 1.94 μm effectively means that the weak signal is lost in noise and interference which may be regarded as a black level saturation where the black level itself is highly dependent on the local environment. This is true even where, as is conventional, the infra-red signal is pulsed or chopped to enhance selectivity in the detection process.

SUMMARY OF THE INVENTION

The present invention is predicated upon the concept of not measuring at 1.94 μm, or to be more precise in practical terms, not measuring in a narrow band centred on that wavelength, but measuring in an adjacent band where absorption is present but is attenuated (that is enhanced transmission) with respect to the absorption peak at 1.94μm. Such an adjacent band thus enables the detection of radiation representing much higher water content before the black saturation level is reached. Conveniently for paper, the measurement band lies in the range 1.76-1.87 μm and the sort of filter ordinarily used for defining the reference wavelength at 1.83 μm can now be used to define the absorption measurement band. Investigation has shown that the 1.83 μm wavelength is not a stable reference where very high water contents are concerned. Effectively, at high water contents the 1.94 μm absorption band (which appears as a trough in a spectrographic trace) widens in wavelength so that even wavelengths outside the normally accepted limits of the band show a measurable degree of absorption though at a substantially lower level than at the centre wavelength of 1.94 μm. This is further discussed below.

If the water content is sufficiently high that 1.83 μm no longer provides a stable reference, then to perform the desirable ratio type measurements, it is now necessary to use a wavelength other than 1.83 μm for the reference and investigation has shown that for paper the 1.7 μm wavelength may be used for this purpose since the web remains relatively transparent at this wavelength even at high water content.

Broadly stated the present invention provides in one aspect apparatus for measuring the water content of a material over a predetermined range and having a source of infra-red radiation for directing at the material, detector means for such radiation and at least first and second filters for selecting radiation for detection at a first wavelength band at which the detected radiation is affected by water content and a second wavelength band at which the detected radiation is substantially unaffected by water content respectively, whereby first and second signals are produced in dependence upon the radiation detected at said first and second wavelength bands respectively, and means responsive to said first and second signals to derive a signal having a value representing the water content, characterised in that said first filter has a significant response at a wavelength offset from the peak of the absorption band so that the absorption detected at the first wavelength band is substantially attenuated with respect to the absorption at the peak, and in that said second filter has a response at a wavelength removed from said first wavelength band and substantially independent of water content over the predetermined range.

In another aspect the invention provides a method of measuring the water content of a material using the absorption spectrum of the material, including moisture therein, in the infra-red where the spectrum includes an essentially water-dependent absorption band, and in which method infra-red radiation is directed onto the material and selective detection is performed at a measurement wavelength band and a reference wavelength band, and the absorption (or transmissivity) of the material at the measurement wavelength is expressed by the radiation detected at the measurement wavelength referred to that detected at the reference wavelength, wherein:

said measurement wavelength band has a significant portion thereof offset from the peak absorption wavelength of said water-dependent absorption band such that absorption at the measurement wavelength is substantially attenuated with respect to that at the peak wavelength; and said reference wavelength is remote from said absorption band and is substantially unaffected by the moisture in the material.

It will be appreciated that whether a scatter type or transmission type of measurement is employed, the wavelength selection can be effected by placing the filters in the path portion following the material, or in the path portion preceding the material where effectively the filters create an infra-red source of selected bandwidth at each selected wavelength. The detection can be made by a single detector where filters are successively and repeatedly interposed in the path or by a respective filter detector combination in association with a beam splitter in the case where the filters are in the path portion following the material.

With particular regard to the measurement of water content in paper-making, it is generally preferred to have the first or measurement wavelength offset to the shorter wavelength side to avoid interference by the cellulose absorption band on the longer wavelength side. The measurement band may be defined by a narrow-band filter of say 0.03 μm bandwidth (which as mentioned is that typically used in current IR gauges), positioned in the spectral region 1.76–1.87 μm. It will be appreciated that the absorption as compared with the peak absorption at 1.94 μm decreases as the band is selected shorter in wavelength. Narrow bandwidth filters are generally preferred for the better noise immunity they provide.

For a moderate water content range it may be satisfactory to place the measurement waveband nearer toward 1.87 μm in which case measurement at or a little below the shorter wavelength end of the quoted range may still be sufficiently stable to be used as a reference, though 1.7 μm could also be used in this case. For high water content, where measurement may be made at or in the vicinity of 1.83 μm or less, then the 1.7 μm wavelength is used for the reference.

The apparatus and method of the invention may find application in a paper-making machine of the kind comprising in succession a Foudrinier wire on which the web is formed; a press section for removing water from the web; and a dryer section for drying the web to a relatively low moisture content: or in a paper-making machine including a coater followed by a dryer section: or in a coating machine having a coater followed by a dryer section. In all these cases, the apparatus or method may be applied to monitor the web at a location preceding the outlet end of the dryer section. Heretofore, it has not been considered possible to satisfactorily use IR gauges at such locations.

In selecting filters for the measurement and reference wavelengths, it is preferred that the ratio of the signal obtained from the reference filter to that obtained from the measurement filter does not exceed a value of about ten, and still more preferably of about three. This assumes the filters are of similar bandwidth and performance differing only in their centre wavelengths.

BRIEF DESCRIPTION OF THE DRAWINGS

The invention and its practice will be further described with reference to the accompanying drawings in which.

Figure 1:
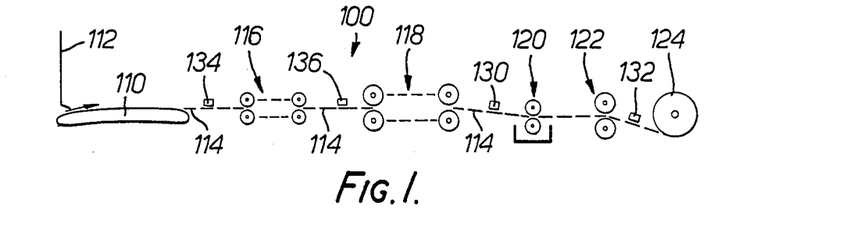
FIG. 1 shows diagrammatically successive stages of a paper-making machine for coated paper.

Referring to FIG. 1, the machine 100 comprises a Foudrinier wire section 110 onto which feedstock is fed from a headbox 112. The web (indicated by dash line 114) formed on the wire passes through the rolls of a press-section 116 which removes a substantial quantity of water from the web. The web then passes into the rolls of the main drying section 118 from which it emerges with a relatively low moisture content and passes, in this example, into a size press 120 to receive a surface coating. On leaving the size press the web goes through the rolls of a second dryer 122 which restores the moisture content to about the same level as it had when leaving the main drying section and the web is then reeled-up at 124.

It is conventional practice in a paper-making machine such as shown in FIG. 1 to provide scanning gauges to measure moisture content at the dry end of the machine, that is at one or more locations following the main dryer section. For example an infra-red scanning gauge may be movably supported on a beam extending normally to the web path to perform repetitive scanning across the web at the exit from the main dryer section 118 as shown at 130 or after the second dryer 122 as shown at 132. Such gauges are typically required to measure a moisture content in the range of 5–10% as already discussed. However, as already discussed it has not been previously considered possible to use an infra-red gauge at the wet end of the machine preceding the main dryer section 118 to measure, with accuracy, the total water content of the web, and hence calculate the moisture ratio. As already discussed the moisture ratio may lie in the range 1–6(corresponding to a moisture content of 50–85.7%). Thus it has not been considered possible to use such gauges to monitor the web immediately on leaving the wire as indicated at 134 or even on leaving the press section as indicated at 136 where the water content has already been reduced. In the case where the main dryer section 118 is divided with intermediate smoothing rolls, the moisture ratio is still likely to have a value up to about 1 (corresponding to a moisture content of 50%). Thus in general it would not be considered possible to satisfactorily use such gauges at any point preceding the output end of the main dryer section 118.

Figure 2A:
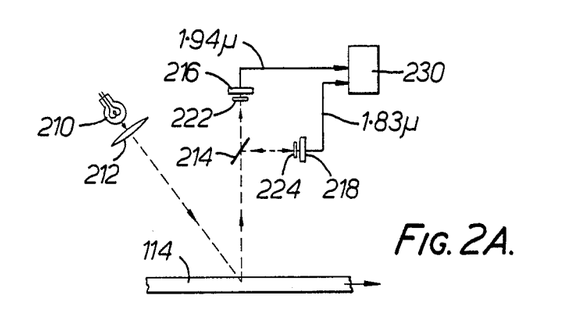
FIG. 2A shows in simplified diagrammatic form a scatter-type gauge for measuring moisture content.
Figure 2B:
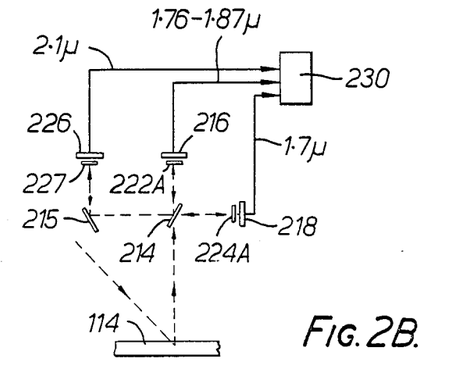
FIG. 2B shows the detector portion of the gauge modified in accord with this invention.

In order to understand how an infra-red gauge can be used at the wet end of the machine, it is necessary to show how present gauges operate at the dry end. This will be done with reference to FIGS. 2 and 3.

FIG. 2A shows by way of example a scatter type gauge 200 providing measurement at two wavelengths. A wideband infra-red (IR) source 210, i.e. an under-run filament lamp, with an associated IR lens 212 directs radiation at an angle of incidence of about 10° onto a relatively small area, say 50 mm. square, of the web. The IR radiation returned from the web passes to a partially transparent IR mirror 214, by which it is split into two paths to impinge on two detectors 216 and 218. The radiation to which these detectors respond is in two selected wavebands determined by narrow-band infrared interference filters 222 and 224 respectively interposed before the detectors. In accord with conventional practice, the filter 222 limits the response of detector 216 to radiation at the water absorption band of 1.94 $\mu$m, that is the filter response is centred at the peak absorption wavelength: the filter 224 limits response of detector 218 to the reference band at 1.83 $\mu$m which is normally considered to be unaffected by water or cellulose. The signals from the two detectors are applied to an electronic processing circuit 230 which ratios the signal from detector 216 with reference to that from detector 218 to provide an output that is a measure of moisture content. The procedures described so far are conventional and will not be described in further detail here.

Figure 3:
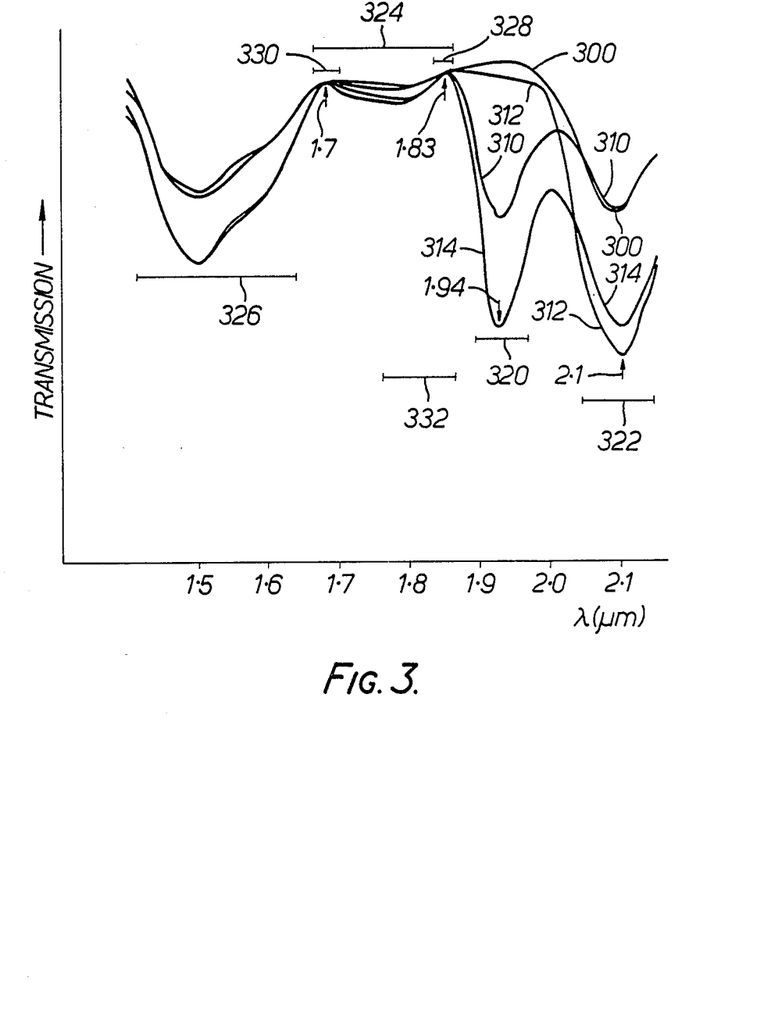
FIG. 3 shows a typical spectrograph in the infra-red showing the absorption spectrum of a sample of paper at different moisture contents.

Looking now at FIG. 3, the effects of the narrow-band filter responses can be better understood with reference to typical spectrograms 300, 310, 312 and 314 taken over the infra-red range in question on four samples of paper web. These spectrograms are based on tests conducted with a high-resolution infra-red spectrometer. The abscissa is wavelength in microns: the ordinate could represent transmittance or reflectance depending on the type of measurement made - transmissive or scatter respectively.

The spectrograms 300 and 310 are taken over the range 1.0 to 2.2 $\mu$m for two samples of a light paper, spectrogram 300 relating to an "oven dry" sample and spectrogram 310 relating to an "air dry" sample having a moisture content of about 7%. Spectrograms 312 and 314 are for samples of a heavier paper that are also "oven dry38 and "air dry" respectively. It will be seen that with the heavier weight paper, the higher water content is shown by the lower transmittance or reflectance (higher absorption) at the band centred on 1.94 $\mu$m. Similar curves could be obtained with papers of like weight but of different formation leading to different effective mean path lengths within the web.

Looking at the spectrograms generally, apart from the water absorption band 320 at 1.94 $\mu$m, there is a nearby cellulose absorption band 322 on the longer wavelength side, which is centred at about 2.1 $\mu$m. At this wavelength the two curves 310 and 312 for the light paper and the two curves for the heavier paper come substantially together since the different water contents are not "visible" at this wavelength.

On the shorter wavelength side there is a plateau 324 of little infra-red absorption which at still shorter wavelength leads to another less well-defined absorption band 326 at about 1.55 $\mu$m. It will be noted that this band is neither as sharp (in bandwidth) nor as deep as the 1.94 $\mu$m absorption band, nor is it as clearly specific to water content as is the band at 1.94 $\mu$m. In the intervening plateau region it is common practice to use the low absorption band 328 (by water or cellulose) that occurs at 1.83 $\mu$m as a reference, though it will be noted that at the shorter wavelength side of the plateau 324 more remote from band 320 is another stable band 330 that can equally be used as a reference.

These bands are utilised in the instrument of FIG. 2A by selecting the water content filter 222 to the peak of absorption band 320 at 1.94 $\mu$m; and the reference filter 224 to the band 328 at 1.83 $\mu$m. It should be noted that the pass-bands of the filters is not to be confused with the spectral bands indicated rather generally in FIG. 3. The filter pass-bands are discussed more fully below with reference to FIGS. 4 and 5.

Such gauges work satisfactorily at the dry end of the paper-making machines, i.e. at positions 130 and 132 in FIG. 1. As already discussed they are not satisfactory at the wet end. The reason for this can be seen from FIG.

3. The transmissivity or reflectance shown at the 1.94 μm wavelength is inversely related to absorption. The detector signal from detector 216 is a measure of transmissivity or reflectance and decreases rapidly with increasing water content. Curve 310 represents a water content of only about 5 gms/m². Even for a light weight paper the water content at the wet end of the machine would be not less than some several times this value giving a virtually total absorption. Measurement at this level is impracticable because any small signal available is lost in noise and interference so that the relevant detector 216 would be measuring the residual background, itself a highly unstable and variable quantity.

It has been now realised that a measurement of high water content can be achieved by moving the response of the filter 222 from the absorption peak at 1.94 μm to the shorter wavelength side of the band in a region 332 between 1.76 and 1.87 μm. The selection of specific filter pass-bands is discussed later. Following investigation of the spectroscopic response at high water content it has been discovered that the stable reference point at 1.83 μm is not as stable as previously thought. Effectively the absorption response illustrated in FIG. 3 broadens out at high water contents and some variation with water content is shown at 1.83 μm.

At moderate water contents—that is above the values accurately measurable by the conventional apparatus but below the highest levels of water contents set out above—the absorption at or adjacent the short wavelength end of the quoted range may still be sufficiently little affected by the water present that it can be used as a reference, the measurement band being placed toward or at the longer wavelength end. It will be appreciated that the transitions are gradual not absolute. However, at high water content where the spread of the absorption band clearly affects 1.83 μm or lesser wavelengths then an alternative reference well away from the quoted range becomes increasingly necessary. A stable reference can be established at about 1.7 μm (1.68 μm) within the band 330 which is unaffected by high water content. Clearly a choice of 1.7 μm for the reference wavelength is suitable for all ranges of water content measurement.

Figure 4:
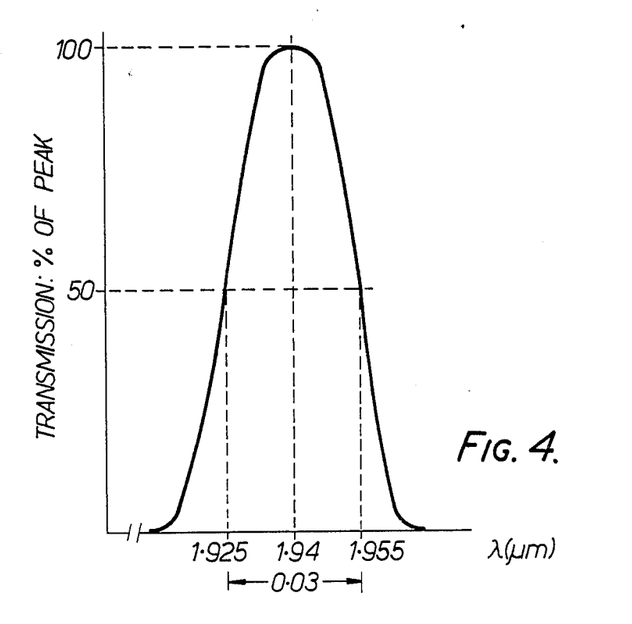
FIG. 4 shows the passband curve of a typical narrow-band filter.

In order to show how filters having a response offset from 1.94 μm can be used in the measurement of high water contents, reference will now be made to FIGS. 4 and 5.

The filters used in practice for apparatus such as shown in FIG. 2A are interference filters having a narrow pass-band. The pass-band response is generally bell-shaped. FIG. 4 shows a typical pass-band curve for such a filter. It is exemplified at 1.94 μm and having a typical bandwidth at 50% of maximum transmission (the value for which bandwidth is normally quoted) of 0.03 μm. Thus the major part of the spectrum passable through the filter has a wavelength between 1.925 and 1.955 μm. This bandwidth is also typical of the narrow-band filters used at 1.83 or 1.7 μm; or at 2.1 μm if a cellulose measurement is made.

Figure 5:
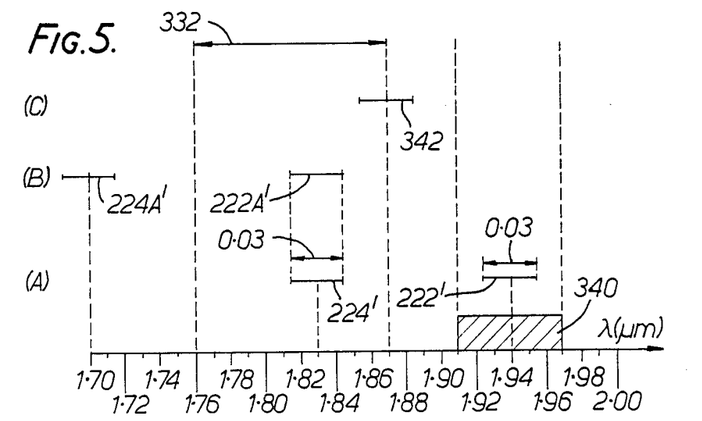
FIG. 5 shows on a wavelength diagram the positioning and bandwidth of various filters that may be employed in the practice of the invention.

The relative positions of the filter passbands in the spectrum of FIG. 3 may be better appreciated from the diagrams of FIG. 5 which show various passbands in relation to the spectral region around the 1.94 μm water absorption band.

Diagram (A) relates to the apparatus of FIG. 2A showing the 0.03 μm bandwidth 222' of narrow-band filter 222 centred on 1.94 μm. This centering on the absorption peak enables adequate sensitivity to be obtained on paper at the dry end of a paper machine to obtain the greatest change in the ratio of the outputs from detectors 216 and 218 for a small change in water content. The passband of the reference filter is shown at 224' centred at 1.83 μm.

However for paper at the wet end of the machine (after the wire or press sections, or at least preceding the outlet end of the main dryer section), the absorption is so high at the pass-band 222' that as explained any slight signal becomes lost in noise and effectively the paper web becomes opaque at this wavelength.

At high water contents the band over which the paper appears to be opaque extends as indicated by the shaded area 340 in FIG. 5, being here exemplified as extending from about 1.91 to 1.97 μm.

An ability to measure high absorption can be restored by having a filter that provides detection at one or more portions of the absorption curve seen in FIG. 3 that is offset from the peak of absorption band 320. There are various ways in which this may be done.

One way is to use a narrow-band filter in the general range of 1.76 to 1.87μm, centre wavelength, as indicated by 332 on FIGS. 3 and 5. One example shown at (B) in FIG. 5 is to use the 1.83 μm filter as the water content filter 222A', using 1.7 μm as a reference filter wavelength 224A'. Such an arrangement would enable very high water contents to be measured. As will be seen from diagram (A) of FIG. 5, there is a substantial spectral gap between the 1.83 μm filter pass-band and the band 340 in which the paper is effectively opaque at high water content. An alternative offset arrangement, is shown in diagram (C) of FIG. 5 in which a narrow-band filter having a pass-band 342 is positionable at the higher wavelength end of the range 332 between band 340 and the "reference" at 1.83 μm. Thus a filter centred at 1.87 μm with a bandwidth of 0.03 μm would provide a greater sensitivity of detection for moderately high water contents than would the 1.83 μm filter. If this is considered insufficiently stable, a 1.7 μm filter for the reference channel can be used. These examples show how a narrow-band filter can be offset from the 1.94 μm peak absorption to provide useful measurement at high water content in paper, the offset being preferably on the short wavelength side to avoid any effect of the cellulose absorption band on the long wavelength side.

FIG. 2B illustrates the adaptation of the detector arrangement of the apparatus of FIG. 2A in accord with the present invention. In FIG. 2B the reference filter 224A has its response at 1.7 μm and the main detector filter 222A has its response at 1.83 μm, or more generally in the range 1.76 to 1.87 μm, and preferably each is a narrow-band filter, e.g. 0.03 μm. The narrower filters assist in reducing the total noise content in the detected signal. This adaptation is in accord with diagram (B) of FIG. 5.

In choosing reference and measurement filter wavelengths with a scatter-type of gauge, it is preferred that the ratio of the output signal from the reference filter 224A to that from the measurement filter 222A is not in excess of about ten, and preferably not in excess of three. This is because the low absorption at the reference wavelength means the web is substantially penetrated by the infra-red radiation whereas, if the comparative output at the longer measurement wavelength is too far reduced relative to the reference value, this is an indication of less penetration and that measurement is being made effectively in too shallow a surface zone.

Figure 6:
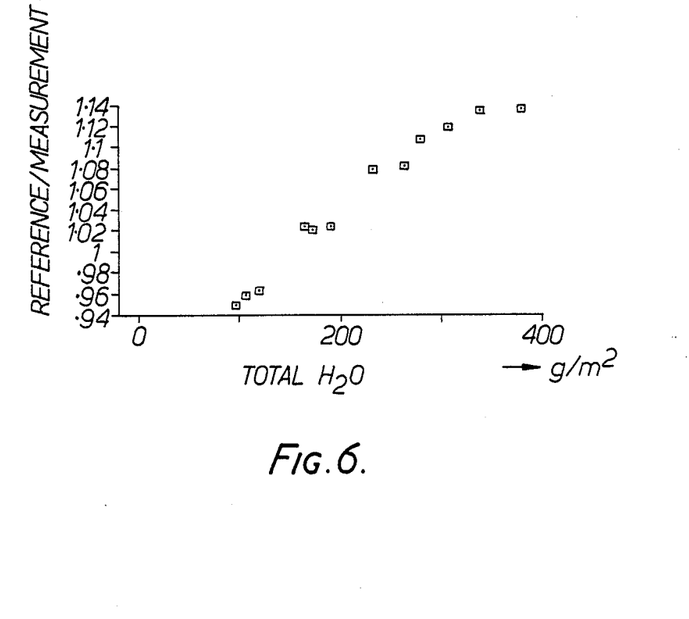
FIG. 6 is a graph illustrating a test measurement made on a range of papers with a gauge in accord with the invention.

FIG. 6 is a graph plotting the results of tests made on a range of papers of various weights with one IR gauge adapted in accord with FIG. 2B using a narrow-band filter at 1.83 μm as the measurement filter and a 1.7 μm reference. The graph shows the grammage of water as the abscissa against the ratio of the signals from detectors 218 and 216. The ratio values shown on the ordinate axis are themselves of no particular significance except that the values below unity are ascribed to instrument characteristics and the general downward slope of the IR spectrum toward the longer wavelength end and which some instruments compensate for. This slope is eliminated from the spectrum of FIG. 3 in order to more clearly demonstrate the features of interest in relation to the present invention. The graph illustrates the fact that an essentially linear relationship exists between the ratio output and water grammage up to 400 g/m$^2$ and it is believed that the relationship will continue to higher grammages of water. Furthermore the measurement of water grammage is substantially unaffected by the dry weight of the sheet. Thus the adapted apparatus has demonstrated the ability, thought not previously possible, to provide useful measurements at very high water content. A practical test on a paper-making machine used to make tracing paper has used a gauge modified in accord with FIG. 2B as so far described to satisfactorily measure water grammages at the wet end of the machine in the range of 100 to 210 g/m$^2$ and thus greatly in excess of the 25 g/m$^2$ value heretofore considered to be the upper limit.

It is considered that the technique disclosed herein of offsetting the main detector filter response from the peak of the IR spectral band used in measurement is of general utility where a material having a high water content is to be measured. Examples already mentioned are textiles and other materials in sheet or web form or particulate or granular materials that are moved along a conveyor and thus resemble a web in this respect.

It will be appreciated that for other materials, the water absorption band at 1.94 μm will be substantially unaffected, provided that the material itself does not have an absorption band of its own overlapping the water absorption band. Assuming that the material has a characteristic absorption band (i.e. a specific band such as the cellulose absorption band for paper) separated from the water absorption band, then a material weight measurement can also be achieved for use in calculating the output as moisture content, that is percentage water by weight. In the nature of the spectroscopic response, there will also be for most materials a wavelength substantially unaffected by water content, and preferably by the material itself, which can be used to obtain a reference.

With other materials, where the material itself does not have an IR absorption band close to 1.94 μm or has such a band on the shorter wavelength side, then the measurement filter may be placed on the longer wavelength side in the latter case or on either side in the former. The choice of filter placement offset from the peak at 1.94 μm is done in accord with the criteria described. One is looking for wavelengths at which absorption is not effectively total for water grammages in excess of 25 and preferably in excess of 100.

FIG. 2B shows an addition to the adaptation of the FIG. 2A apparatus by providing for paper a cellulose measurement channel using an additional mirror 215, and a detector 226 preceded by a narrow-band filter 227 having a response centred at 2.1 μm. The mirror 215 effectively cooperates with interference filter 224' which effectively acts as a mirror at 2.1 μm. While the measurement of cellulose absorption is itself known, in order to be able to calculate moisture content or to apply a correction factor as in above-mentioned specification 2 044 433, the provision of such a IR measurement channel is particularly advantageous at high water content because the measurements made with β-gauges used for the dry weight measurement of paper are rendered less accurate where a high water content is present.

While the foregoing description has particularly referred to the adaptation of a scatter type of gauge, it will be appreciated that the teachings of the invention are equally applicable to transmission type gauges. In one transmission type gauge a single detector is used and a rotating filter holder is provided that sequentially and repetitively interposes the desired filters in the IR path. The presentation of the filters is correlated to the processing of the signal from the single detector to obtain water absorption, cellulose absorption and reference signals. Thus such apparatus can also be adapted by locating filters in accord with the teachings of the invention at the appropriate places in the filter holder.

I claim:

1. Apparatus for measuring the water content of a material over a predetermined range and having a source of infra-red radiation for directing at the material, detector means for such radiation and at least first and second filters for selecting radiation for detection at a first wavelength band at which the detected radiation is affected by water content and a second wavelength band at which the detected radiation is substantially unaffected by water content respectively, wherein first and second signals are produced in dependence upon the radiation detected at said first and second wavelength bands respectively, and means responsive to said first and second signals to derive a signal having a value representing the water content, the improvement wherein the first wavelength band at which said first filter responds has a center wavelength of approximately 1.83 microns, wherein said second filter wavelength band is removed from said first wavelength band to provide a response that is substantially independent of water content over the predetermined range and has a center wavelength of approximately 1.7 microns, and wherein the moisture ratio of the material lies in the range of 1 to 6.

2. Apparatus as claimed in claim 1 in which said first filter is a narrow-band filter.

3. Apparatus as claimed in claim 2 in which said first filter has a bandwidth of 0.03 microns.

4. Apparatus as claimed in claim 1 including a dryer section for drying the web to a relatively low moisture contact and in which the infra-red source, filters and the detectors arrangement is arranged in a gauge positioned adjacent the web to provide a measure of the water content of the web, and wherein the gauge is mounted adjacent the web at a location preceding the outlet end of said dryer-section.

5. Apparatus as claimed in claim 1 including a coater followed by a dryer section in which the infra-red source, filters and the detector arrangement in a gauge positioned adjacent the web to provide a measure of the water content of the web, and wherein the gauge is mounted adjacent the web at a location preceding the outlet end of said dryer section.

6. A method of measuring the water content of a material using the absorption spectrum of the material, including moisture therein, in the infra-red where the spectrum includes an essentially water-dependent absorption band, and in which method infra-red radiation is directed onto the material and selective detection is performed at a measurement wavelength band and a reference wavelength band, and the absorption of the material at the measurement wavelength band is expressed by the radiation detected at the measurement wavelength band referred to that detected at the reference wavelength band, wherein said measurement wavelength band has a center wavelength of approximately 1.83 microns;

said reference wavelength band is remote from said measurement wavelength band and has a center wavelength of approximately 1.7 microns wherein radiation in said reference wavelength band is substantially unaffected by the moisture in the material; and the moisture ratio being measured lies in the range of 1 to 6.

7. A method as claimed in claim 6 in which said measurement wavelength band is defined by a narrow-band filter.

8. A method as claimed in claim 7 in which said filter has a bandwidth of 0.03 microns.

9. A method of on-line measurement of the water content of the web in the wet end of a paper-making machine at a location preceding the outlet of the dryer section in a paper-making machine having in succession a Fourdrinier wire on which a web is formed, a press section for removing water from the web and a dryer section for drying the web to a relatively low moisture content, comprising the steps of:

directing infra-red radiation onto the web at a location where the moisture ratio lies between 1 and 6;

selectively detecting the infra-red radiation at a measurement wavelength band and a reference wavelength band, each defined by a respective filter;

expressing the absorption of the material at the measurement wavelength band by the radiation detected at the measurement wavelength band referred to that detected at the reference wavelength band, wherein said measurement wavelength band has a center wavelength of 1.83 microns; and wherein said reference wavelength band has a center wavelength of about 1.7 microns and is remote from said measurement wavelength band wherein radiation in said reference wavelength band is substantially unaffected by the moisture in the material.

10. A method for on-line measurement of the water content of a web in a paper machine at a location preceding the outlet of the dryer section comprising the steps of:

directing infra-red radiation onto the web at a location where the moisture ratio lies between 1 and 6;

selectively detecting the infra-red radiation at a measurement wavelength band and a reference wavelength band, each defined by a respective filter;

expressing the absorption of the material at the measurement wavelength band by the radiation detected at the measurement wavelength band referred to that detected at the reference wavelength band, wherein said measurement wavelength band has a center wavelength of about 1.83 microns; and wherein said reference wavelength band is remote from said measurement wavelength band and has a center wavelength of about 1.7 microns wherein radiation in said reference wavelength band is substantially unaffected by the moisture in the material.

11. A method for on-line measurement of the water content of a web in a paper machine at a location preceding the outlet of the dryer section comprising the steps of:

directing infra-red radiation onto the web at a location where the moisture ratio lies between 1 and 6;

selectively detecting the infra-red radiation at a measurement wavelength band and a reference wavelength band, each defined by a respective filter;

expressing the absorption of the material at the measurement wavelength band by the radiation detected at the measurement wavelength band referred to that detected at the reference wavelength band, wherein said measurement wavelength band has a center wavelength of about 1.83 microns; and wherein said reference wavelength band is remote from said measurement wavelength band and has a center wavelength of about 1.7 microns wherein radiation in said reference wavelength band is substantially unaffected by the moisture in the material.

12. A paper-making machine of the type comprising a headbox for providing a feedstock comprising a suspension of cellulose-based fibrous material in water, a wire section for draining water from feedstock delivered from the headbox to initiate formation of a web, a press section for receiving and extracting moisture from said web to reduce the moisture content of the web, and a main dryer section to further reduce the moisture content of the web, the web in its path between the wire section and the main dryer section having a water-to-dry-weight ratio in the range of 1–6, a moisture measurement station located along the web path between the wire section and the main dryer section, said station comprising an infrared source to direct infrared radiation onto the web, first and second infrared detectors for receiving radiation from the source as attenuated by the web to provide first and second signals, and means for processing the second signal with reference to the first to provide an output signal, and first and second infrared filters associated with said first and second detectors respectively to select the infrared wavelengths to which the detectors respond, said first filter providing a pass-band at a wavelength of about 1.7 microns that is substantially unaffected by the moisture content of the web, said second filter providing a pass-band at a wavelength of about 1.83 microns that is affected by the water-to-dry-weight ratio of the web being in the range of 1–6, wherein said output signal represents a measure of the moisture content of the web in said range.

13. A paper-making machine as claimed in claim 12 in which the water content of the web in the paper-making machine in its path between the wire section and the main dryer section lies from above 25 up to 600 grams/square meter and in which said moisture measurement station comprises a third detector and a third filter associated therewith for receiving radiation from the source attenuated by the web, said third filter providing a passband at a wavelength affected by cellulose in the web, and said processing means processing said second and third signals with reference to the first to provide an output signal representing the moisture content of the web.

14. In a paper-making machine of the type comprising a headbox for providing a feedstock comprising a suspension of cellulose-based fibrous material in water, a wire section for draining water from feedstock delivered from the headbox to initiate formation of a web, a press section for receiving and extracting moisture from said web to reduce the moisture content of the web and a main dryer section to further reduce the moisture content of the web, the web in its path between the wire section and the main dryer section having a water content in the range of 25–600 grams/square metre, a moisture measurement station located along the web path between the wire section and the main dryer section, said station comprising an infrared source to direct infrared radiation onto the web, first and second infrared detectors for receiving radiation from the source as attenuated by the web to provide first and second signals, and means for processing the second signal with reference to the first to provide an output signal, and first and second infrared filters associated with said first and second detectors respectively to select the infrared wavelengths to which the detectors respond, said first filter providing a pass-band at a wavelength of about 1.7 microns that is substantially unaffected by the water content of the web, said second filter providing a pass-band at a wavelength of about 1.83 microns that is affected by the water content of the web being from above 25 up to 600 grams/square meter, wherein said output signal represents the water content of the web in said range in the paper machine at said moisture measurement station.

15. In an apparatus for measuring the water content of a material over a predetermined range and having a source of infra-red radiation for directing at the material, detector means for such radiation and at least first and second filters for selecting radiation for detection at a first wavelength band at which the detected radiation is affected by water content and a second wavelength band at which the detected radiation is substantially unaffected by water content respectively, whereby first and second signals are produced in dependence upon the radiation detected at said first and second wavelength bands respectively, and means responsive to said first and second signals to derive a signal having a value representing the water content, the improvement comprising the material having a water content in the range of 25–600 g/m$^2$, the first wavelength band at which said first filter responds has a center wavelength of approximately 1.83 microns, wherein said second filter wavelength band is removed from said first wavelength band to provide a response that is substantially independent of water content over the predetermined range and has a center wavelength of approximately 1.7 microns.

16. A method of on-line measurement of the water content of the web in the wet end of a paper-making machine at a location preceding a dryer section in a paper-making machine having in succession a Fourdrinier wire on which a web is formed, a press section for removing water from the web and a dryer section for drying the web to a relatively low moisture content, comprising the steps of:
directing infra-red radiation onto the web in the wet end of the paper-making machine;
selectively detecting the infra-red radiation at a measurement wavelength band and a reference wavelength band, each defined by a respective filter;
expressing the absorption of the material at the measurement wavelength band by the radiation detected at the measurement wavelength band referred to that detected at the reference wavelength band,
wherein said measurement wavelength band has a center wavelength of 1.83 microns; and
wherein said reference wavelength band is remote from said measurement wavelength band and is centered at about 1.7 microns radiation in said reference wavelength band is substantially unaffected by the moisture in the material.

17. A method for on-line measurement of the water content of a web in a paper machine at a location preceding the outlet of the dryer section comprising the steps of:
directing infra-red radiation onto the web at a location where the water content is in the range of 25–600 g/m$^2$;
selectively detecting the infra-red radiation at a measurement wavelength band and a reference wavelength band, each defined by a respective filter;
expressing the absorption of the material at the measurement wavelength band by the radiation detected at the measurement wavelength band referred to that detected at the reference wavelength band,
wherein said measurement wavelength band has a center wavelength of about 1.83 microns; and
wherein said reference wavelength band is remote from said measurement wavelength band and has a center wavelength of about 1.7 microns wherein radiation in said reference wavelength band is substantially unaffected by the moisture in the material.

18. Apparatus for measuring the water content of a material over a predetermined range and having a source of infra-red radiation for directing at the material, detector means for such radiation and at least first and second filters for selecting radiation for detection at a first wavelength band at which the detected radiation is affected by water content and a second wavelength band at which the detected radiation is substantially unaffected by water content respectively, wherein first and second signals are produced in dependence upon the radiation detected at said first and second wavelength bands respectively, and means responsive to said first and second signals to derive a signal having a value representing the water content, the improvement wherein the first wavelength band at which said first filter responds has a center wavelength of approximately 1.83 microns, wherein said second filter wavelength band is about 1.7 microns, and is removed from said first wavelength band to provide a response that is substantially independent of water content over the predetermined range, and wherein the material has a water content of above 25 up to 600 g/m$^2$.

* * * * *